(12) United States Patent
Titus

(10) Patent No.: US 9,592,042 B2
(45) Date of Patent: Mar. 14, 2017

(54) SURGICAL DEVICE AND METHODS

(75) Inventor: Augustine Titus, Bolton (GB)

(73) Assignee: Central Manchester University Hospitals NHS Foundation Trust (GB)

( * ) Notice: Subject to any disclaimer, the term of this patent is extended or adjusted under 35 U.S.C. 154(b) by 362 days.

(21) Appl. No.: 13/640,731

(22) PCT Filed: Apr. 8, 2011

(86) PCT No.: PCT/GB2011/000541
§ 371 (c)(1),
(2), (4) Date: Oct. 11, 2012

(87) PCT Pub. No.: WO2011/128622
PCT Pub. Date: Oct. 20, 2011

(65) Prior Publication Data
US 2013/0030253 A1    Jan. 31, 2013

(30) Foreign Application Priority Data
Apr. 13, 2010   (GB) .................................. 1006079.6

(51) Int. Cl.
*A61B 1/32* (2006.01)
*A61B 17/02* (2006.01)
(Continued)

(52) U.S. Cl.
CPC ......... *A61B 17/0281* (2013.01); *A61M 29/02* (2013.01); *A61B 17/0218* (2013.01); *A61B 2017/00557* (2013.01)

(58) Field of Classification Search
CPC ......... A61B 1/3132; A61B 1/313; A61B 1/32; A61B 17/3423; A61B 17/3431;
(Continued)

(56) References Cited

U.S. PATENT DOCUMENTS 4,083,369 A    4/1978  Sinnreich
5,431,173 A    7/1995  Chin et al.
(Continued)

FOREIGN PATENT DOCUMENTS

GB          1006079       9/1965
WO       WO 9725094       7/1997
(Continued)

OTHER PUBLICATIONS

International Search Report and Written Opinion issued by the European Patent Office, dated Aug. 2, 2011, for related International Application No. PCT/GB2011/000541; 5 pages.
(Continued)

*Primary Examiner* — Lynnsy Summitt
(74) *Attorney, Agent, or Firm* — Faegre Baker Daniels LLP

(57) ABSTRACT

The present invention relates to a device for creating a working space within a human or animal body. The device comprises an outer wall which is configurable to adopt a non-expanded condition and an expanded condition. When the outer wall is in said expanded condition it defines a hollow body having an inner cavity in communication with an orifice for location adjacent a working site within the body such that, in use, said working site can be visualized and/or accessed via said inner cavity and said orifice.

18 Claims, 8 Drawing Sheets

(51) Int. Cl.
*A61M 29/02* (2006.01)
*A61B 17/00* (2006.01)

(58) Field of Classification Search
CPC ............ A61B 17/3439; A61B 17/0218; A61B 17/3462; A61B 17/0281; A61B 17/02; A61B 2017/00557; A61B 2017/320048; A61B 2017/3445; A61B 2017/3466; A61B 2017/00287
USPC .................................................. 600/184–246
See application file for complete search history.

(56) References Cited

U.S. PATENT DOCUMENTS

| | | | |
|---|---|---|---|
| 5,450,843 A * | 9/1995 | Moll .................. | A61B 17/0218 600/207 |
| 5,575,759 A * | 11/1996 | Moll .................. | A61B 17/0218 600/207 |
| 5,667,520 A | 9/1997 | Bonutti | |
| 5,685,826 A | 11/1997 | Bonutti | |
| 5,688,526 A | 11/1997 | Okamoto et al. | |
| 5,860,997 A | 1/1999 | Bonutti | |
| 5,865,728 A | 2/1999 | Moll et al. | |
| 5,976,079 A | 11/1999 | Volz et al. | |
| 6,361,543 B1 | 3/2002 | Chin | |
| 6,432,121 B1 | 8/2002 | Jervis | |
| 6,605,037 B1 * | 8/2003 | Moll .................. | A61B 17/0218 600/204 |
| 7,037,317 B2 | 5/2006 | Hermann et al. | |
| 7,300,448 B2 | 11/2007 | Criscuolo et al. | |
| 2003/0216611 A1 | 11/2003 | Q. Vu | |
| 2004/0015182 A1 | 1/2004 | Kieturakis | |
| 2004/0097792 A1 | 5/2004 | Moll et al. | |
| 2004/0158261 A1 * | 8/2004 | Vu .................. | A61B 17/00234 606/114 |
| 2006/0173483 A1 | 8/2006 | Kieturakis et al. | |
| 2008/0058854 A1 | 3/2008 | Kieturakis et al. | |
| 2008/0081951 A1 * | 4/2008 | Frasier .............. | A61B 17/0218 600/207 |
| 2009/0082634 A1 | 3/2009 | Kathrani | |
| 2013/0178710 A1 * | 7/2013 | Suh .................. | A61B 17/0293 600/205 |

FOREIGN PATENT DOCUMENTS

| | | |
|---|---|---|
| WO | WO 9734532 | 9/1997 |
| WO | WO 2005102185 | 11/2005 |
| WO | WO 2005104959 | 11/2005 |
| WO | WO 2009050717 | 4/2009 |

OTHER PUBLICATIONS

United Kingdom Intellectual Property Office Search Report, dated Aug. 2, 2010, for related UK application GB 1006079.6, 3 pages.
Ortiz-Oshiro et al., Gasless laparoscopic cholecystectomy is not more time-consuming, Surgical Endoscopy Ultrasound and Interventional Techniques, Sep. 4, 2001, 1448-1451, 15.
Talwar et al., Randomized Controlled Trial of Conventional Carbon Dioxide Pneumoperitoneum versus Gasless Technique for Laparoscopic Cholecystectomy, JK Science, 2006, 73-78, vol. 8—No. 2.
Gurusamy et al., Abdominal lift for laparoscopic cholecystectomy, Cochrane Database of Systematic Reviews, 2012, 1-53, Issue 5, John Wiley & Sons, Ltd.
Gurusamy et al., Day-case versus overnight stay for laparoscopic cholecystectomy, Cochrane Database of Systematic Reviews, 2008, 1-45, Issue 3, John Wiley & Sons, Ltd.
Bretthauer et al., NORCCAP (Norwegian colorectal cancer prevention): a randomised trial to assess the safety and efficacy of carbon dioxide versus air insufflation in colonoscopy, Gut, 2002, 604-607, No. 50.
Wolfe et al., Laparoscopic Cholecystectomy a Remarkable Development, JAMA, Mar. 27, 1991, 1573-1574, vol. 265—No. 12.
Wang et al., Gasless laparoscopy for benign gynecological diseases using an abdominal wall-lifting system, Journal of Zhejiang University Science B, 2009, 805-812, vol. 10—No. 11.
Kruschinski, The pneumoperitoneum—a continuing mistake in laparoscopy ?, Der Frauenarzt, May 2000, 1-16.
Henny et al., Laparoscopic surgery Pitfalls due to anesthesia, positioning, and pneumoperitoneum, Surgical Endoscopy and Other Interventional Techniques, Jul. 28, 2005, 1163-1171, 19.
Barbabellaatje, Screen Shots of "How to 'quickly' make an Origami Magic Ball," YouTube, Oct. 17, 2009, 6 pages, video available online at http://www.youtube.com/watch?v=tGhcTwIJ4Es&feature=related.

* cited by examiner

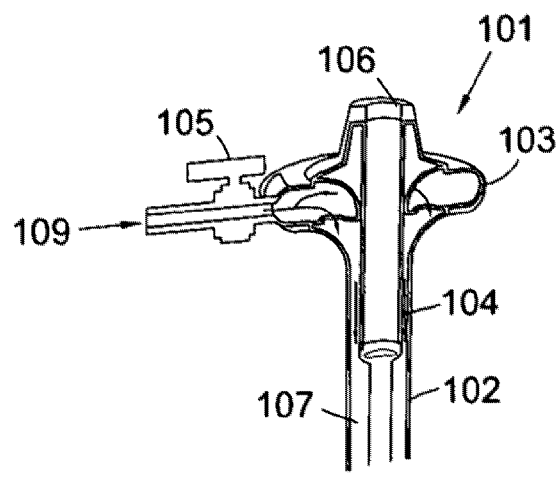
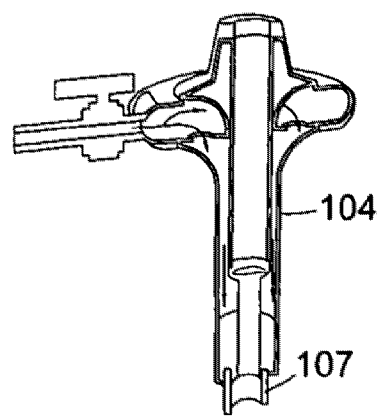
Fig. 9A   Fig. 9B
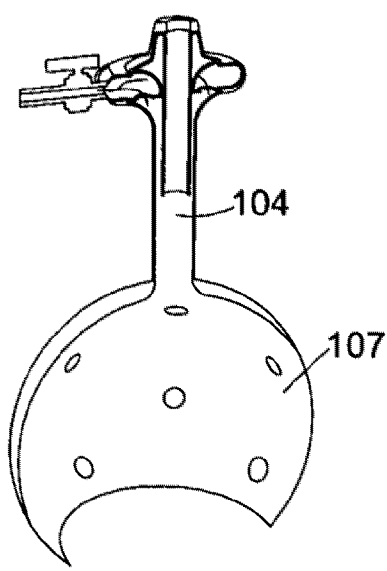
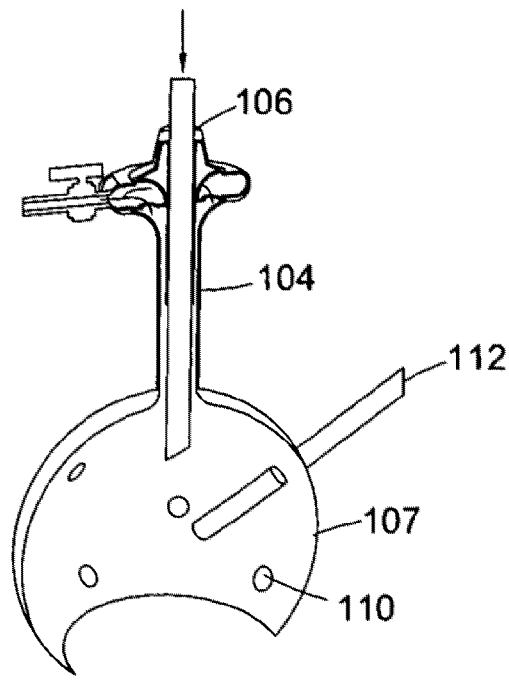
Fig. 9C   Fig. 9D

SURGICAL DEVICE AND METHODS

The present application is a National Stage of International Application No. PCT/GB2011/000541, filed Apr. 8, 2011 which claims the benefit of Great Britain Application No. 1006079.6, filed Apr. 13, 2010, the disclosures of which are expressly incorporated by reference herein.

The present invention relates to a device for creating a working space within a body, particularly, but not exclusively, during laparoscopic procedures. The present invention also relates to methods of employing the device in, for example, intra-abdominal surgery, as well as other medical procedures.

Laparoscopic procedures are becoming more popular due to their non-invasive nature. For example, laparoscopic surgery is the main method of treating symptomatic gallstones and is used in many intra-abdominal surgical procedures, including hernia repairs and kidney surgery. Its use in gynaecological procedures and other pelvic procedures is increasing. However to enable good visibility and operating space within the abdomen, and for the sake of safety, additional procedures are necessary immediately prior to the surgery itself.

The most common method of creating a working space in the abdomen is to create a Carbon Dioxide ($CO_2$) pneumoperitoneum. This method consists of inserting a port into the abdominal space to which a tube is connected, through which the $CO_2$ is administered. The $CO_2$ increases the intra-abdominal pressure causing the abdominal wall to stretch and expand, thereby creating a larger working space through which to access the working site.

Issues associated with this method include ensuring there is a good seal between the body and $CO_2$ ports so that a continuous supply of $CO_2$ can be provided throughout the procedure otherwise the gas will escape and the abdominal wall collapse. The introduction of a pressurised gas has additional complications and side effects on a percentage of the population, most commonly the elderly. The most common side effect of a pneumoperitoneum and a raised intra-abdominal pressure is an elevated diaphragm leading to collapse of the bases of the lungs with chest infections. $CO_2$ absorption can lead to metabolic acidosis and hypercapnia, as well as hypoxaemia in the tissue and increased post-operative pain. Further problems include hypothermia, and hyperventilation, and operative complications such as the risk of the pneumoperitoneum collapsing at the moment of a haemorrhage leading to dangerous loss of vision of the operative site. The use of $CO_2$ insufflation in combination with suction can cause difficulties during surgery. The use of suction can lead to losses in effective intra-abdominal pressure, while insufflation using $CO_2$ can reduce the effectiveness of suction procedures affecting the surgeon's ability to visualise the operating site. Suction systems are routinely used in laparoscopic procedures to remove blood and other surgical debris and to clear smoke arising from the use of lasers and electrosurgical devices. The limited availability of medical grade $CO_2$ in less well developed countries also currently limits the application of laparoscopic procedures in these areas.

There is therefore a need for an alternative to $CO_2$ insufflation which can create space within a body to provide a sufficiently large working environment for laparoscopic procedures but with minimal side effects and operational advantages over current standard of care. The current alternative for creating abdominal space is the gasless use of an Abdominal Wall Lifter. These are mechanical devices that fit under the abdominal wall and are lifted vertically by an external crane. These cause high amounts of stress to the abdominal tissues, can be cumbersome in the operating field and may cause cosmetic damage to skin.

An object of the present invention is to obviate or mitigate one or more of the aforementioned problems with current methods for creating a working space within a body.

According to a first aspect of the present invention there is provided a device for creating a working space within a human or animal body, the device comprising an outer wall which is configurable to adopt a non-expanded condition and an expanded condition; in said expanded condition said outer wall defining a hollow body having an inner cavity in communication with an orifice for location adjacent to a working site within the body such that, in use, said working site can be visualised and/or accessed via said inner cavity and said orifice.

A second aspect of the present invention provides a method for creating a working space within a human or animal body using a device comprising an outer wall which is configurable to adopt a non-expanded condition and an expanded condition, the method comprising introducing the device into said human or animal body with the outer wall in said non-expanded condition and then expanding the outer wall such that it adopts said expanded condition and defines a hollow body having an inner cavity in communication with an orifice located adjacent to a working site within the human or animal body such that said working site can be visualised and/or accessed via said inner cavity and said orifice. This method may be employed just for observation of the working site without a surgical or therapeutic procedure being performed, or may be employed to facilitate access to the working site to enable a surgical or therapeutic procedure to be performed thereon, in which case the procedure will usually be accompanied with observation of the working site by one or more methods as known to the skilled person.

A third aspect of the present invention relates to a method of surgery involving a method for creating a working space within a human or animal body according to the second aspect of the present invention and performing a surgical procedure, such as intra-abdominal surgery, laparoscopic surgery and/or a cholycystectomy.

A fourth aspect of the present invention provides a gynaecological procedure comprising a method for creating a working space within a human or animal body according to the second aspect of the present invention and performing a gynaecological operation. This method will typically involve the insertion of the expandable device into a natural orifice of the patient rather than via any form of incision. That being said, in certain applications the method may involve the making of an incision through which the device is inserted into the patient.

The device according to the present invention employs a novel technology that can provide a sufficiently rigid structure to move and support surrounding tissue or organs and a clear working space through which to visualise and access a working site, while being sufficiently compact to facilitate insertion via a small incision or orifice in the skin.

The outer wall may be displaceable between the expanded and non-expanded states using any appropriate stimulus, such as by mechanical means and/or inflation. The transition between the two states may be reversible or non-reversible. It is preferably reversible so as to facilitate insertion into the patient in the non-expanded or contracted condition so that it can be introduced via a small incision or orifice, expanded following insertion to enable the intended operation to be performed at the working site and then contracted back to the non-expanded condition for removal from the patient.

Preferably the outer wall is arranged to be inflatable so as to expand and adopt the expanded condition. The structure of the outer wall of the device may take any desirable form but in a preferred embodiment the outer wall comprises at least an inner and an outer layer of material. The outer wall may of course include as many layers of material or "skins" as desired, such as three, four or more and so is not limited to a "double-skinned" embodiment including just an inner and outer layer of material. In this multi-layer embodiment, the outer wall is inflatable by the introduction of a fluid in between said inner and outer layers of material. The term "fluid" without further qualification is used herein to refer to a gas or liquid. A preferred gaseous fluid for use in inflating the device of the present invention is air, while a preferred liquidus fluid is saline. It will however be appreciated that any suitable fluid may be used. The inner and outer layers are preferably concentrically arranged with respect to one another. The layers may be connected together using, for example, welding, to ensure a space or spaces of the desired size, shape and relative location are defined between the layers to receive the inflation fluid so that the outer wall of the device expands to assume the intended final shape following inflation.

In a first preferred embodiment, such as that shown in FIG. 1 below, substantially the whole of said outer wall consists of said inner and outer layers of material. Most preferably the outer wall consists of a single inner layer and a single outer layer such that the outer wall can be considered as being "double-skinned" substantially across its entire surface. In this embodiment, the inner and outer layers are connected together in a carefully predetermined manner so as to define a single space between the "skins" of the outer wall which is of uniform thickness for receipt of the inflation fluid. This arrangement has the advantage of enabling the entire space between the "skins" to be accessed by the inflation fluid via a single fluid inlet as shown in FIG. 1. Regardless of whether the inflation fluid is introduced via a single fluid inlet or multiple inlets, this arrangement of a single inflatable space is also advantageous in that a consistent inflation pressure can be applied across the entire outer wall of the device thereby ensuring that the outer wall inflates and expands in a uniform manner.

Inflation of the outer wall of the device may be achieved using a manually operated pump or an electrically operated pump of any appropriate design as would be known to the skilled person. A manual pump, such as fluid filled syringe, may be preferred in some situations since they are already likely to be available in the operating room. However, potential disadvantages include the fact that they may be more time consuming to use, may require repeated filling from the fluid source (e.g. a saline bag) and/or may be difficult to control so as to accurately limit the inflation pressure supplied to the device. Advantages of an electric pump include the ability to effect automatic fluid delivery to the device upon receipt of a predetermined signal, inflation pressures can be easily and accurately controlled, it is quick and relatively simple—requiring minimal input from the surgeon, the removal of fluid in an accurate and controlled manner may be easily achieved. A disadvantage of such a system is that a suitable pump may not already be available within the operating theatre.

In an alternative preferred embodiment, said outer wall is comprised of a plurality of individually inflatable areas or segments.

In a still further embodiment, predefined regions of said outer wall consist of said inner and outer walls of material. Sections of the outer wall in between said predefined regions may consist of a single layer of material and/or are non-inflatable. Alternatively or additionally, sections of the outer wall in between said predefined regions may consist of multiple layers of material.

The outer wall may comprise a plurality of separate predefined regions, at least one of which adopts an elongate tubular shape upon the introduction of said fluid in between said inner and outer layers of material. Said predefined regions may be separate to one another or may be in fluid communication so as to define a single elongate tubular shape upon the introduction of said fluid in between said inner and outer layers of material. The single elongate tubular shape may be straight, i.e. linear, or may be curved to assume a desired shape of sufficient structural strength to support surrounding organs and/or tissue to create the intended working space. By way of example, the single elongate tubular shape may be arranged to assume a generally coiled configuration upon the introduction of said fluid in between said inner and outer layers of material. Optionally, adjacent areas of said coiled tube may be interconnected by one or more supporting member to lend further structural strength to the device and/or to ensure the coil assumes the desired general shape following expansion.

The inflation pressure required to expand the device so that it can perform its intended function may depend upon one or more of the following factors: the structure of the outer wall of the device and/or the nature of the inflation fluid, both of which will affect the load-bearing capacity of the device; and the type of procedure being performed and/or the nature of the environment surrounding the intended working site, both of which will contribute to the required load-bearing ability of the device. It is preferred that the outer wall of the device is configured so as to withstand inflation pressures of around 20 to 200 mmHg.

The outer wall may be produced from any appropriate material. Particularly preferred materials include polymeric materials, which are described in more detail hereinbelow. To facilitate visualisation of the working space it is preferred that the outer wall of the device is substantially transparent. The device may take any convenient shape, but in a preferred embodiment the outer wall of the device is configured such that upon expansion said hollow body has a generally spherical shape.

For reasons discussed in more detail below the outer wall of the device preferably defines one or more apertures for the introduction of instruments and the like.

In a preferred embodiment a region of the outer wall adjacent the orifice is connected to a draw-cord which is operable to close said orifice. This embodiment can be employed to remove sections of tissue or organs for example for further testing or investigation. A specific exemplary embodiment is described below with reference to FIGS. 10 and 11.

It will be appreciated that the device according to the first aspect of the present invention is eminently suitable for use in the method for creating a working space within a human or animal body according to the second aspect of the present invention. In the second aspect, expansion of the outer wall of the device is preferably effected by inflating said outer wall. It is preferred that the outer wall of the device comprises at least an inner and an outer layer of material and inflation of the outer wall is effected by the introduction of a fluid, such as air or saline, in between said inner and outer layers of material. As discussed above, the inflation pressure should be selected depending upon a number of different factors but a preferred range is around 20 to 200 mmHg. It may be advantageous to employ a relatively warm inflation fluid so as to reduce the possibility of causing damage to tissue or organs adjacent to the device once inserted into the patient body. Preferably the inflation fluid is introduced at a temperature of around 15 to 45° C., more preferably around 20 to 40° C., and most preferably around body temperature, e.g. around 35 to 40° C. It may be desirable to employ an inflation fluid that possesses a temperature that is elevated above body temperature, e.g. around 40 to 50° C. so as to warm surrounding tissue and/or organs in the vicinity of the working site. It may also be desirable in certain applications to employ an inflation fluid that possesses a temperature below body temperature to cool surrounding tissue and/or organs. By way of example, this may be desirable to counteract hyperthermia, i.e. raised body temperature, due to a fever or some other condition. In this case, it may be desirable to use an inflation fluid at a temperature of around 5 to 15° C.

In a preferred exemplary embodiment the device is inserted into the desired area of the patient, e.g. the abdomen in an uninflated and therefore unexpanded condition. Once in position adjacent the intended working site, a fluid, e.g. air or saline, is introduced into the walls of the device so that it inflates and expands so as to define a hollow, preferably double-skinned, part-sectioned sphere. During expansion the device moves or retracts adjacent organs and/or tissue away from the working site so as to define a working space adjacent to the working site to facilitate visualisation and/or access to the working site. The device is part-sectioned so as to define a cut-out region in a part of the device, e.g. the base of the sphere, which is located so as to overlie the intended working site and thereby create a well-defined and convenient working environment including the working space for instruments and the working site, and excluding the surrounding normal tissue thus improving safety.

The device preferably defines an aperture in a proximal section of a wall of the device for insertion of a laparoscope and a distal section of the wall of the device preferably defines a further aperture arranged to overlie the intended working site. In preferred embodiments the further aperture in the distal section of the device wall closely surrounds the intended working site and in doing so effectively defines the actual working site visualised and/or accessed during the subsequent procedure. Typically a laparoscope will be inserted through the centre of the device and will be used in the centre of the hollow internal cavity defined by the walls of the device to provide visual feedback of the operation at the working site. It is preferred that the wall of the device defines one or more additional holes to facilitate insertion of additional laparoscopic instruments into the working environment created by the hollow sphere. Once the operation has been completed the device is then preferably evacuated of fluid and the device retracted from the body. The device may be a single use, disposable product, or may be re-usable.

In an embodiment of the device a drawstring or the like is fitted within the wall of the device in a region circumscribing the cut-out section which overlies the working site. The drawstring can be drawn away from the device so as to close the cut-out section of the device, thereby sealing the device and turning it into a bag in which tissue or organs, e.g. the gallbladder, can be simply and effectively removed from the working site.

In a preferred embodiment, the device comprises a double-skinned, partially-sectioned hollow sphere which defines an internal working space through which the working site can be both visualised and accessed as opposed to the use of a transparent inflatable balloon which would facilitate visualisation but not internal access to the working site because the space created by inflation of the balloon is ultimately occupied by the balloon itself. While devices for separating and moving tissue within the human body to create a working space or visualise a working site are known, most are based around the concept of mechanically expanding arms, or inflatable balloons to create the space but with the balloon occupying the space that is created. The device of the present invention provides for the first time a means by which a working space can be created through which an operating procedure can be carried out and laparoscopic instruments introduced while at the same time allowing excellent visualisation of the working site. It is envisaged that the device of the present invention may incorporate an illumination system and/or camera to facilitate visualisation of the working site.

The preferred embodiment employing a hollow structure created by the union of the two skins of the double-skinned outer shell preferably defines a partial sphere with a plurality of apertures or orifices to allow the insertion of instruments through the skin at various angles into the working space created within the hollow sphere, thus allowing unimpeded access to the tissues requiring attention at the working site. In some embodiments, it may be preferred only to provide apertures in the proximal half of the hollow sphere, while in other embodiments it may be preferred to provide apertures in the distal half, while in still further embodiments it may be preferred to provide apertures over the whole structure of the device. It will be appreciated that a balance must be achieved between the number of apertures provided in the device and the structural rigidity or strength of the device. The device must be sufficiently strong to be able to support surrounding tissue and/or organs during the intended procedure while still including enough apertures to facilitate the desired level of access to the working site via the working space within the internal cavity defined by the device. In embodiments in which a larger number of apertures are desired it may be preferred to form at least a part of the shell of the device from stronger or more rigid members by selection of appropriate materials and/or by inflating the device to a higher pressure.

A further feature associated with the device of the present invention lies in the ability to employ a relatively warm fluid to inflate the device so as to provide a warming effect to the working environment and thereby prevent hypothermia.

It is anticipated that the amount of disruption that the present invention will cause to the healthcare provider is relatively low. Clinically it will be less of a disruption than the current insufflation using $CO_2$ as there will be no concern that there are leaks and that the pneumoperitoneum will collapse. The amount of $CO_2$ and pressures used in insufflation are monitored, something else that will be obsolete with the gasless methods employing the device of the present invention. Operationally there should be little or no difference. The removal of the requirement for the use of heavy $CO_2$ canisters should prove a significant advantage alone.

Further advantages over $CO_2$ insufflation include improved organ retraction, better ability to use effective suction and no clinical side effects for the patient. The device offers the opportunity to reduce overall healthcare costs by reducing length of stay following minimally invasive surgery. This is due to a potential reduction in complications associated with the current methods such as $CO_2$ induced pneumoperitoneum. The device additionally provides the possibility to increase the number of elective procedures that are carried out on a day case basis, currently only 11.3% of elective cholecystectomies are performed as day-case surgery in the UK.

The device of the present invention is eminently suitable to be used in the operating theatre for use within the abdomen, primarily for Cholycystectomy (gallbladder removal) operations. However there are several other areas within the body where the device could be used, for example in gynaecological operations, in the pelvic region (e.g. the uterus, ovaries, bladder), liver and bowel resections, kidneys, spleen, incisional hernia repairs, arthroscopic procedures (e.g. knee) and transplant kidney removal. Moreover, the device according to the present invention may find application in veterinary surgery, dentistry, thoracic surgery, urologic surgery, ear nose and throat surgery and Natural Orifice Translumenal Endoscopic Surgery (NOTES). A further advantage associated with the device of the present invention is that in view of its construction it is eminently suitable for use in emergency and military applications, such as in a field hospital or on the battlefield itself.

Embodiments of the present invention will now be described, by way of example only, with reference to the accompanying drawings in which:

FIGS. 9A to 9D illustrate steps in the deployment and use of the device according to the first preferred embodiment of the present invention;

Figure 1:
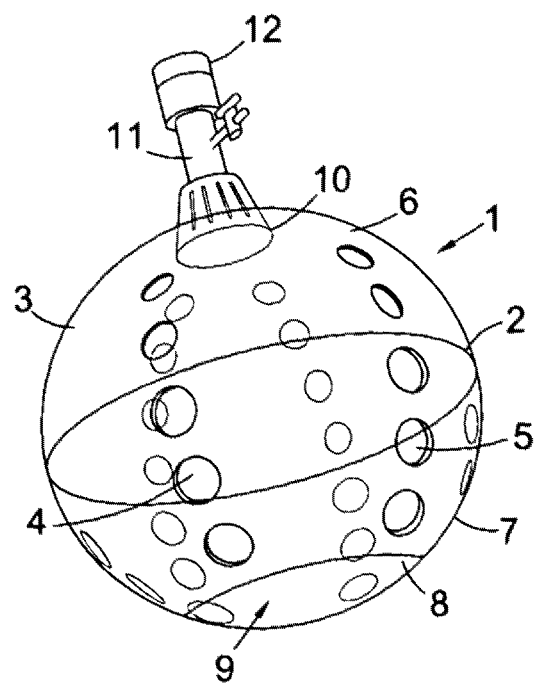
FIG. 1 is an illustration of a device according to a first preferred embodiment of the present invention shown in an expanded condition.

Referring to FIG. 1, there is shown a first preferred embodiment of a device 1 according to the present invention. The device 1 is shown in an expanded state as it would be after insertion during a surgical procedure and comprises a generally spherical body 2 defined by a double-skinned outer wall 3 made of polyurethane polymer or the like. The body 2 does not of course have to be generally spherical but may instead take any desirable shape. It will also be appreciated that the shape of the device body 2 once expanded within the patient's body and retracting and supporting surrounding organs and tissue may not retain exactly the same shape as that shown in FIG. 1, but may instead deform slightly to conform to the optimum load-bearing shape. The spherical outer wall 3 defines a hollow body 2 having a maximum outer diameter in this specific embodiment of around 200 mm and an internal cavity 4 which can be accessed via a plurality of circular apertures 5 defined by the outer wall 3. The maximum outer diameter of the body 2 can take any appropriate value provided it is sufficiently large to create a working space adjacent the intended working site of adequate size to allow the surgeon to access and visualise the working site. It will be appreciated that the optimum size will depend upon a number of factors including the type of procedure being carried out and the size of the patient. The body 2 of the device may therefore have a maximum diameter of around 50 to 300 mm, more preferably around 100 to 250 mm. Devices 1 intended for use in abdominal procedures preferably have a maximum diameter of at least around 200 mm, while devices for use in more specialised areas of the body, such as joints, the pelvis, bladder, uterus etc are preferably smaller with lower maximum diameters following expansion. The embodiment shown in FIG. 1 includes many apertures 5 in both the upper 6 and lower 7 (i.e. proximal and distal) halves of the device body 2. It will be appreciated that any desirable number, size and/or shape of apertures 5 may be provided in just the upper section 6, just the lower section 7 or both the upper and lower sections 6, 7.

As shown in FIG. 1, the lowermost section of the spherical body 2 is sectioned to define a circular cut-out section 8 which defines a relatively large orifice 9 extending through the outer wall 3 of the device 1. The orifice 9 is dimensioned so that once the device 1 is correctly positioned within the patient the orifice 9 overlies the intended surgical working site. In this way, the internal cavity 4 of the device 1 provides a clear and easily accessible laparoscopic working space within the patient through which the working site and pathology can be visualised and accessed by suitable instruments.

The device shown in FIG. 1 further defines a hole 10 in the uppermost section of the spherical body 2 which is connected to a port 11 which serves two functions. First, the port 11 enables a fluid, such as air or saline, to be introduced into the space between the inner and outer skins of the double-skinned outer wall 3 of the device 1 so as to inflate and expand the device 1 following insertion. This is discussed in more detail below in relation to FIG. 9. Second, the port 11 has a suitable connector 12 for the attachment of a laparoscope (not shown) to enable the surgeon to visualise the working space.

Figure 2:
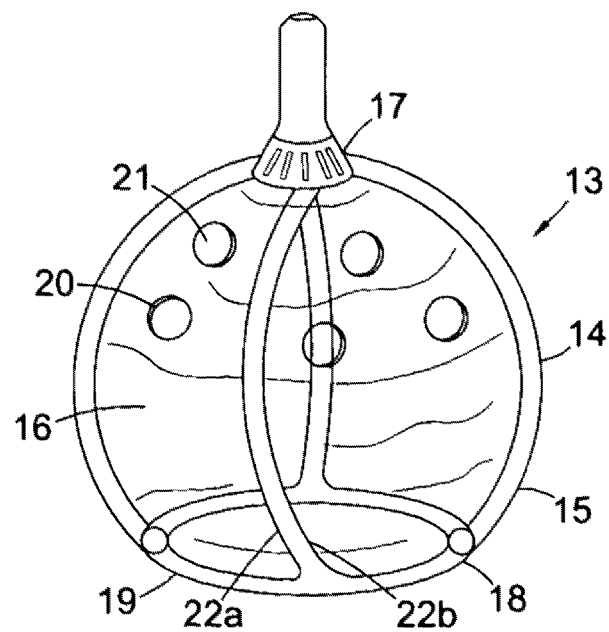
FIG. 2 is an illustration of a device according to a second preferred embodiment of the present invention shown in an expanded condition.

FIG. 2 shows a second preferred embodiment in which the device 13 takes the same general form as that shown in FIG. 1 except that only predefined sub-sections 14 of the outer wall 15 of the device 13 receive fluid to inflate and expand the device 13, with intermediate sections 16 of the outer wall 15 being non-inflatable. The inflatable sections 14 are defined as elongate passages or tubes extending linearly from the top 17 to the bottom 18 of the device 13, i.e. from the inflation port (not shown) proximal to the surgeon to the rim 19 around the cut-out section distal to the surgeon which is intended to encircle the working site. In this way, as fluid is introduced via the port into the tubes 14 the device 13 is caused to expand both radially outwardly and axially from the port towards the working site.

In the embodiment shown in FIG. 2 the intermediate outer wall sections 16 are single skinned and define a plurality of apertures 20 to facilitate access to the internal cavity 21 defined by the outer wall 15 following expansion of the device 13. It will be appreciated that the intermediate sections 16 do not have to be single skinned but may instead be double-skinned if appropriate. By way of example, the entire outer wall 15 may be formed from a sheet of double-skinned polyurethane material and the inflatable tubes 14 defined by pairs of weld lines 22a, 22b or the like spaced across the width of the material. To ensure only the tubes 14 are inflated during use only the proximal ends of the tubes are connected to the fluid delivery line via the port. The tubes 14 and the intermediate sections 16 of the outer wall 15 may be formed of the same material or the tubes 14 may be formed from a first type of material, such as a relatively strong polymeric material capable of withstanding the relatively high inflation pressures required to retain the structural integrity of the device 13, and the intermediate sections 16 formed from a second type of material, such as a thinner or more lightweight material that is strong enough to support surrounding tissue or organs during use but reduces the overall weight and/or volume of the device 13, which may be advantageous when considering storage and deployment of the device 13 via narrow surgical incisions as are common in laparoscopic procedures.

Figure 3:
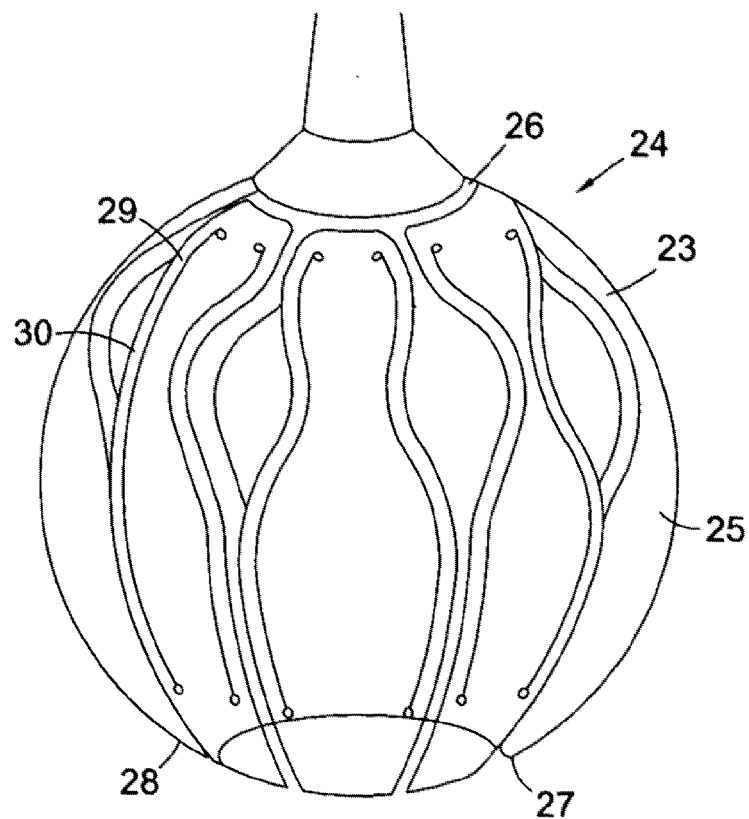
FIG. 3 is an illustration of a device according to a third preferred embodiment of the present invention shown in an expanded condition.

FIG. 3 illustrates a third preferred embodiment wherein the outer wall 23 of the device 24 is defined by a plurality of interconnected segments 25 which expand from a folded state (not shown) by inflation. Each segment 25 is formed from a double-skinned polyurethane polymer or the like and is connected to neighbouring segments 25 by suitable connection means such as welding or interlinking using wires or polymer twines. Each segment 25 may be of the same shape or segments 25 of two or more different shapes may be used to define the desired number, size and shape of apertures through the outer wall 23 of the device 24 to facilitate insertion of instruments. In the embodiment shown in FIG. 3, the outer wall 23 of the device 24 is defined by a plurality of segments 25 all of the same shape which are interlinked around the proximal rim 26 of the device 24 adjacent the inflation port (not shown) and around the rim 27 in the lower section 28 of the device 24 which will circumscribe the working site during use. Reinforcing wires or polymer twines 29 extend along the edge 30 of each segment 25 and interconnect wires or twines running around the upper and lower rims 26, 27.

A manifold (not shown) is provided within the inflation port to ensure that inflating fluid is passed only into the space between the inner and outer skins of the double-skinned wall of each segment 25. A similar manifold arrangement may also be used in other preferred embodiments of the present invention, such as the second preferred embodiment described above to ensure that inflating fluid is passed only into the elongate tubes 14.

Figure 4:
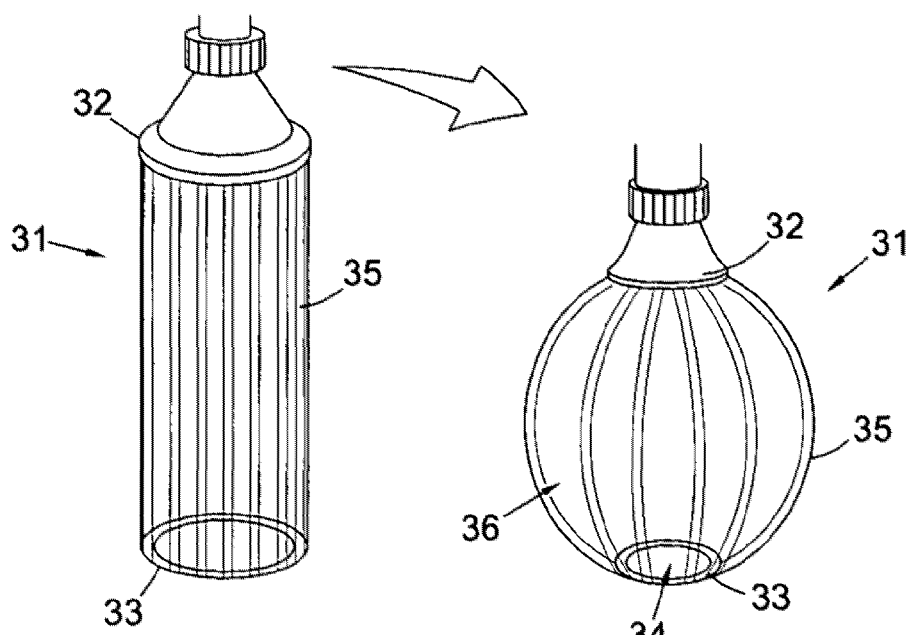
FIG. 4 is an illustration of a device according to a fourth preferred embodiment of the present invention shown in an unexpanded (left) and expanded (right) condition.

A fourth embodiment of the present invention is illustrated in FIG. 4 in which expansion of the device 31 to a substantially spherical state is achieved primarily by twisting or compressing the device 31 about an axis passing through an upper rim 32 of the device 31 connected to a port (not shown) for connection to a laparoscope and a lower rim 33 which defines an orifice 34 intended to surround the working site. The upper and lower rims 32, 33 are interconnected by a plurality of equi-angularly spaced bars 35, which may be solid bars, hollow tubes or wires, constructed from a suitable polymer and/or metal which can deform from being substantially straight during deployment to being curved and/or twisted radially outwardly prior to surgery at the working site. Some or all of the bars 35 may be interconnected by a wall of material (not shown), optionally defining apertures (not shown) for access to the working space 36 within the device 31. Alternatively, neighbouring bars 35 may be linked only at the upper and lower rims 32, 33 of the device 31 and so the space between adjacent bars 35 facilitates access to the working space.

Figure 5:
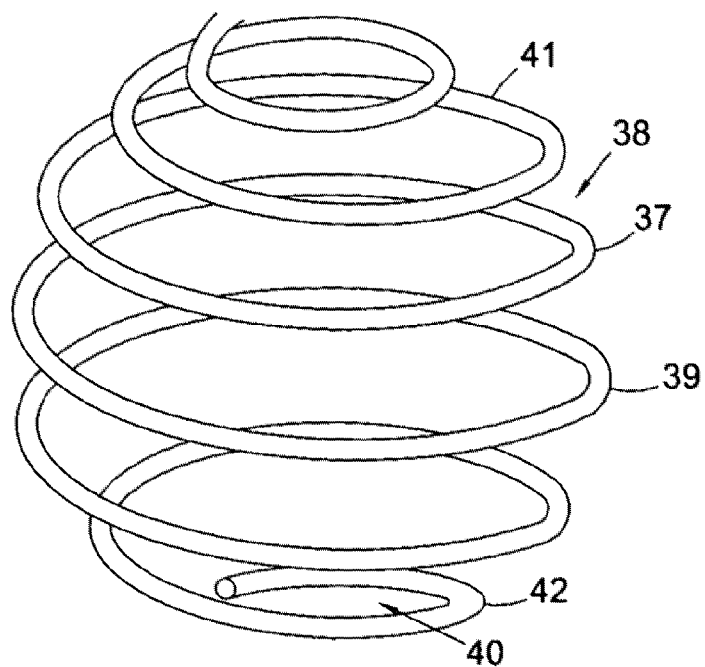
FIG. 5 is an illustration of a device according to a fifth preferred embodiment of the present invention shown in an expanded condition.
Figure 5A:
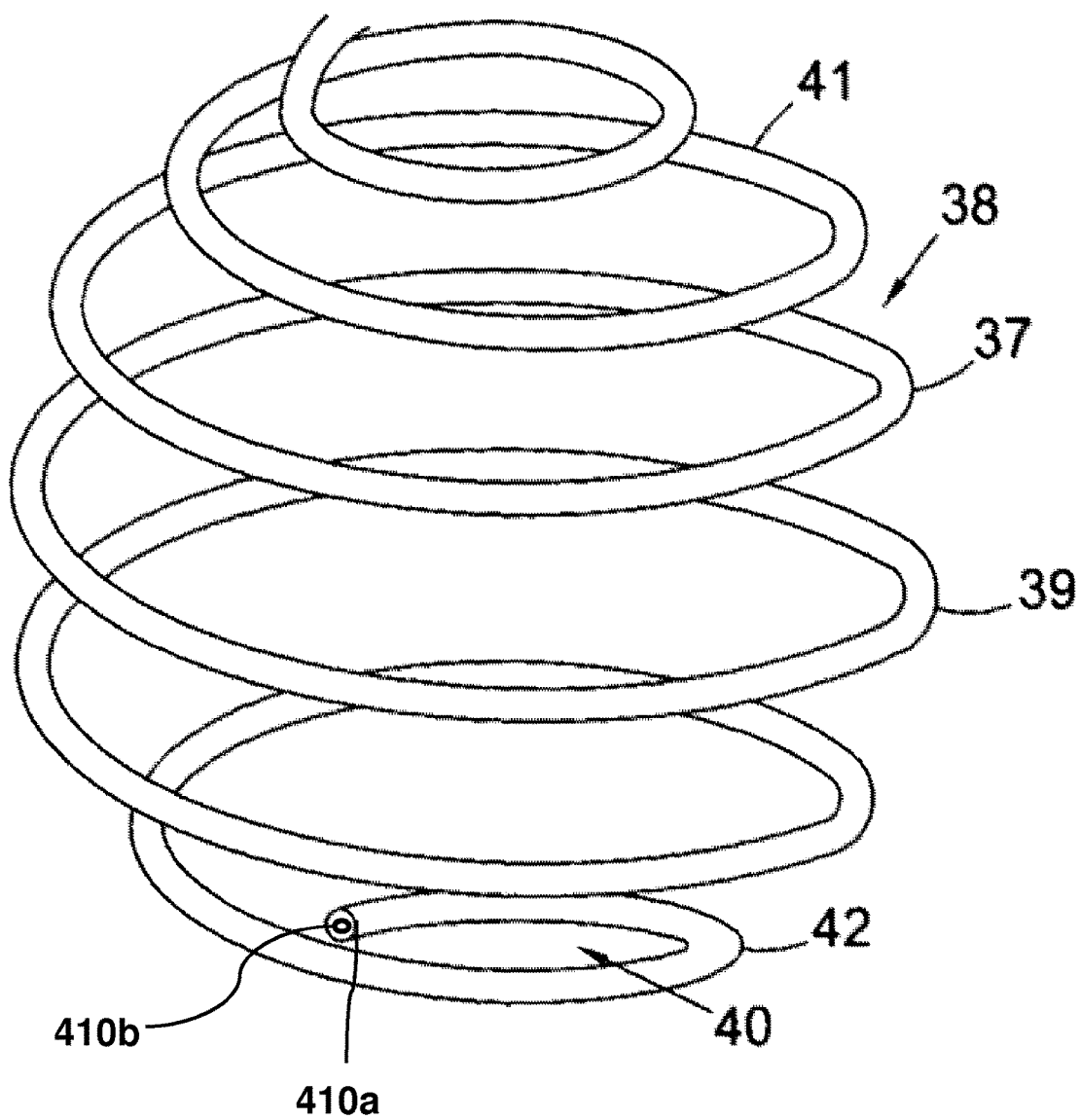
FIG. 5A is an illustration showing additional detail of the device according to the fifth preferred embodiment of the present invention shown in an expanded condition.

A fifth preferred embodiment is shown in FIG. 5 in which the outer wall 37 of the device 38 is defined by a single hollow tube 39 of polyurethane polymer or the like which is formed into a coil or spiral. Prior to insertion the tube 39 is empty and the coil is compressed. Following insertion into the patient a suitable fluid is introduced into the hollow tube 39 thereby causing the coil to inflate and expand to assume the general form of a sphere as in the previous embodiments. The tube 39 is dimensioned appropriately so that following expansion the coil defines a distal orifice 40 which can be arranged to overlie an intended working site. Although not shown in FIG. 5 it may be desirable to incorporate one or more supporting members extending between upper and lower rims 41, 42 of the device 31 to afford resistance to re-compression of the device 31 along an axis connecting the two rims. The supporting members may comprise hollow inflatable tubes, solid bars and/or wires as appropriate. In an alternative (as shown in FIG. 5A), the single elongate tube 39 may be formed of inner 410b and outer 410a layers of material. In this embodiment, the tube 39 may assume a generally coiled configuration upon introduction of fluid in between said inner 410b and outer 410a layers of material.

Figure 6:
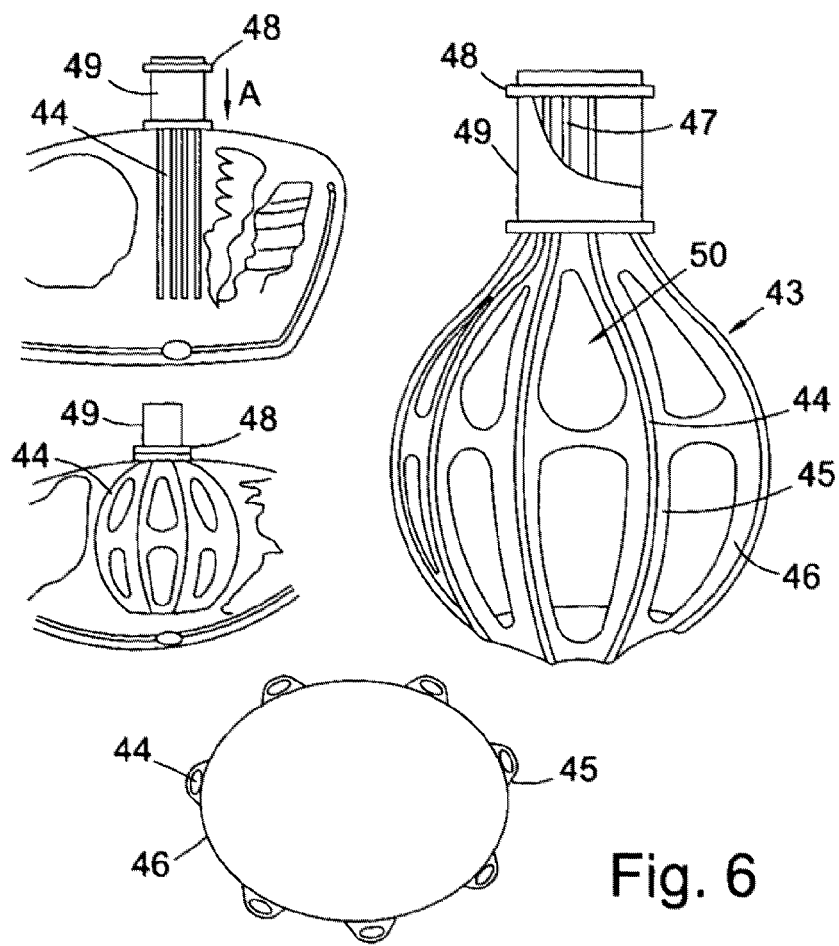
FIG. 6 is an illustration of a device according to a sixth preferred embodiment of the present invention shown in an unexpanded (top left) and expanded (lower and right) condition.

FIG. 6 shows a sixth preferred embodiment of the present invention in which the device 43 incorporates a plurality of relatively rigid elongate rods 44 which are contained within channels or tubes 45 defined by the outer wall 46 of the device 43. The rods 44 are constrained at their distal end 47 (the end nearest the surgeon) within pockets (not shown) connected to a ring 48 which can slide up and down a tube 49, i.e. towards and away from the surgeon in the direction of arrow A, with the tube 49 remaining outside of the patient's body. As the ring 48 is moved away from the surgeon and towards the patient in the direction of arrow A the rods 44 bend outwards away from one another and cause the outer wall 46 of device 43 to expand radially outwardly. It will be appreciated that this design enables the surgeon to accurately control the degree of expansion of the outer wall 46 of the device 43 by adjusting the extent to which the ring 48 is slid down the central tube 49. Apertures 50 for the insertion of instruments are defined between adjacent regions of the outer wall 46 of the device 43.

Figure 7:
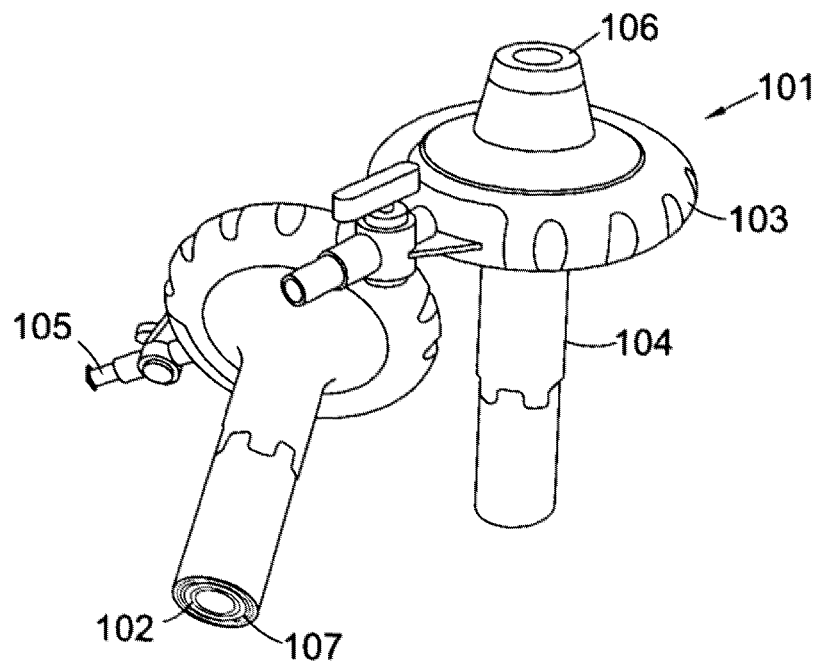
FIG. 7 is an illustration of a device according to a preferred embodiment of the present invention shown in an unexpanded condition.

FIG. 7 shows a pair of devices 101 according to the present invention with the expandable section 102 of the device 101 in a non-expanded condition. Each device 101 comprises a radially extending collar 103 connected to a downwardly extending tubular portion 104. The collar 103 incorporates a port 105 for connection to a source of an inflation fluid, such as air or saline, and a fixture 106 for connection to a laparoscope. The tubular portion 104 is an elongate hollow tube within which is folded or wrapped a sheet of double-skinned polyurethane material 107 which, when inflated with said fluid, expands to assume the hollow spherical shape of the device 1 described above in relation to FIG. 1.

Figure 8:
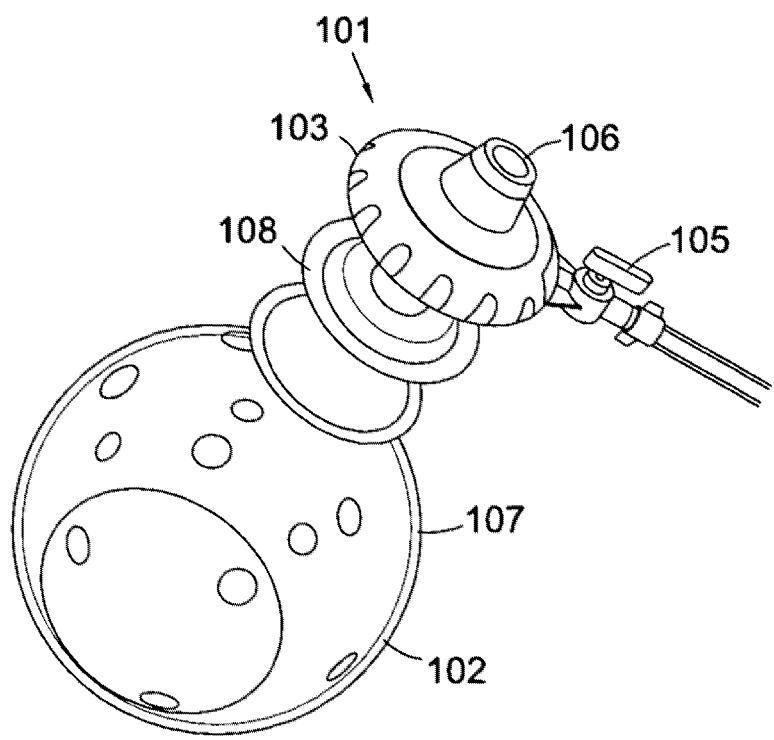
FIG. 8 is an illustration of the device according to the first preferred embodiment in an expanded condition connected to an optional collar designed to provide a seal with tissue surrounding the point of incision.

FIG. 8 shows the device 101 of FIG. 7 following introduction of the inflating fluid via a supply line connected to the port 105 so as to inflate and expand the double-skinned polymer sheet 107 so that it assumes the shape of the device 1 shown in FIG. 1. The device 101 shown in FIG. 8 additionally incorporates a secondary collar 108 located in between the collar 103 including the port and laparoscope fixture 106 and the expandable section 102 of the device 101. The secondary collar 108 is arranged so as to minimise local trauma to the skin of the patient surrounding the surgical incision.

The material from which the expandable outer wall of the device is formed is preferably sufficiently durable to afford resistance to damage from laparoscopic instruments during the surgical procedure. It is preferably translucent or transparent to aid visualisation of the working space via a laparoscope of the like. Moreover, the material should be sterilisable using gamma irradiation at greater than 25 kGray without degradation of material performance. Any welded features incorporated into the construction of the device may be radio frequency welded, for example, to form the sealed spherical shape from two layers of polyurethane film. It is envisaged that "cut and seal" tooling methods may be used to define the various apertures and orifices in the outer wall of the device. Weld features may be incorporated into the tooling and in that way may provide stability to the structure of the device and help maintain its shape when inflated and expanded.

It is preferred that the expandable outer wall of the device is sufficiently conformable so as to be able to collapse into a small volume for deployment through a small, e.g. 10 mm, diameter incision percutaneously, but be substantially free of unwanted folds and creases when inflated.

The device is produced from bio-compatible materials with the ability to meet the relevant aspects of ISO10993 relevant to a product that is used invasively on a temporary basis, i.e. an external device in communication with blood and tissue for less than 24 hours.

The material from which the expandable outer wall of the device is produced should be selected to suit the particular structural embodiment chosen from those described above and the intended application of the device. Preferred materials include polyurethane extruded or blown films without a carrier layer, such as one of the Epurex range manufactured by Bayer, e.g. Walopur® 2102. Alternative materials which may be useful in different applications of the device include polyvinylchloride, polyethylene and latex. The specific thickness of the material forming each skin of a single, double or multi-skinned outer wall of the device can be determined by the skilled person who will appreciate that since these types of film exhibit very high tensile stresses (in the order of 70 MPa at failure) the potential failure mode is anticipated to be weld joints rather than the material given that the anticipated inflation pressures are likely to be in the order of around 20 to 200 mmHg (0.027 MPa).

With regard to the collar to which the expandable outer wall of the device is attached, it is preferred that the collar and expandable wall are connected by a welded construction using ultrasonic tooling comprising 3D sonitrodes and nests to hermetically seal plastic moulded components of the collar and to the material forming the outer wall. Solvent bonding or ultraviolet-activated adhesives are alternative methods of attachment.

The collar may be produced, for example, from Terlux 2802TR by BASF for the base mouldings and Santoprene TPV or Kraiburg's Thermolast K TPE for ovemoulded components.

In FIGS. 9A to 9D there are shown four of the basic steps in deploying and using the device 101 of the present invention as shown in FIGS. 7 and 8. The tubular portion 104 of the device 101 containing the folded expandable sheet 107 is first inserted into an optimum region of the anatomy of the patient, as deduced by the surgeon, adjacent the intended working site either via an incision or a natural body orifice depending upon the surgical procedure being undertaken. The desired position of secondary instruments is also taken into account by surgeon when deciding upon the optimum position for the device 101. An inflation fluid 109, such as air or saline, is then introduced via the port 105 in the collar 103 through the tubular portion 104 into the space between the inner and outer skins of the double-skinned sheet of material 107 (FIG. 9A). As the fluid 100 enters the space within the sheet 107 the sheet 107 begins to inflate and expand downwardly out of the tubular portion 104 towards the intended working site (FIG. 9B). As the sheet 107 escapes the confines of the tubular portion 104 it is freed to expand radially outwardly as well as to continue to expand towards the working site until the space within the double-skinned sheet 107 is filled and the sheet 107 assumes its final substantially spherical form with a plurality of access apertures 110 through the side wall of the sheet and a lowermost circular rim 111 surrounding a cut-away section dimensioned to circumscribe the working site (FIG. 9C). A laparoscope (not shown) can then be introduced through the collar fixture 106 and one or more instruments 112 inserted through the working space via the access apertures 110 to the working site (FIG. 9D).

Figure 10:
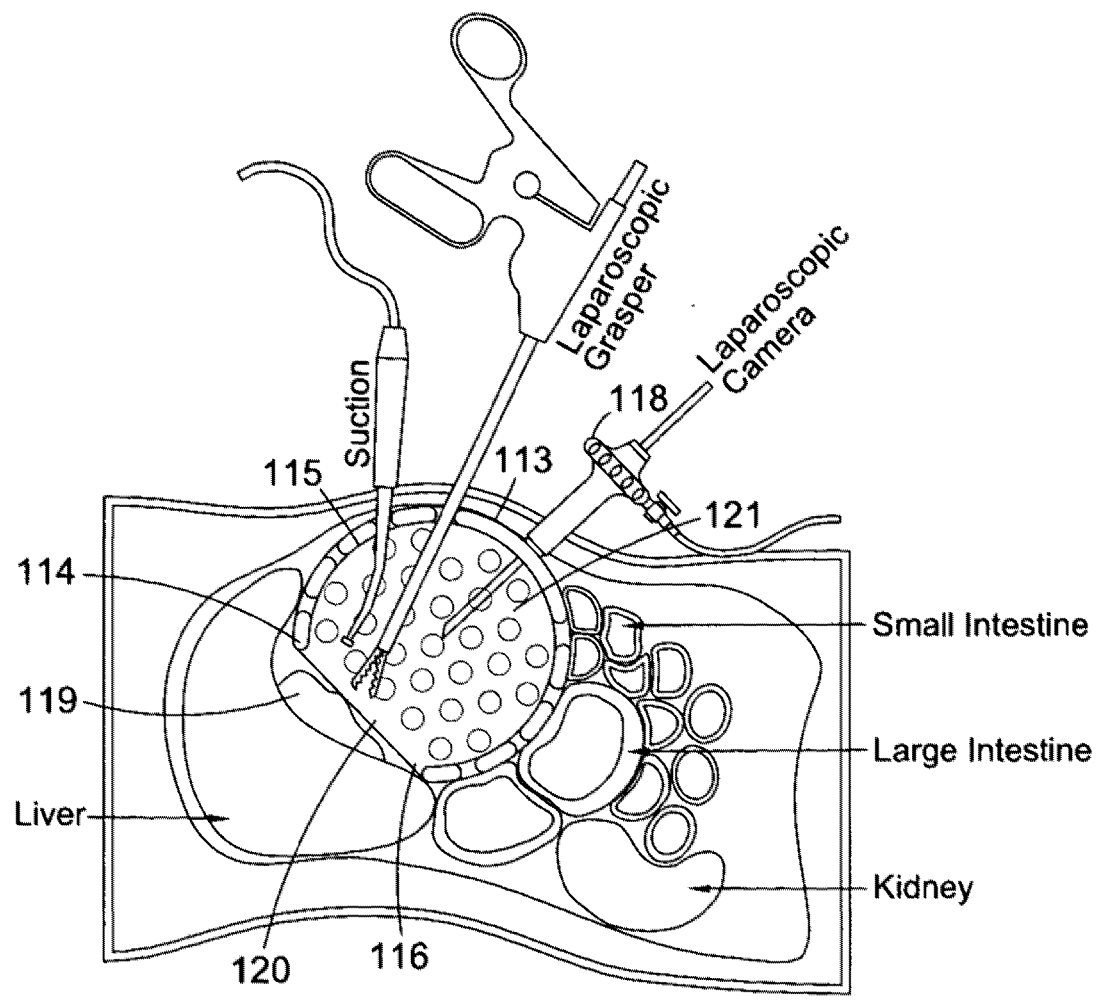
FIG. 10 is a schematic cross-sectional illustration of a device according to a preferred embodiment of the present invention in a cholecystectomy procedure.
Figure 11:
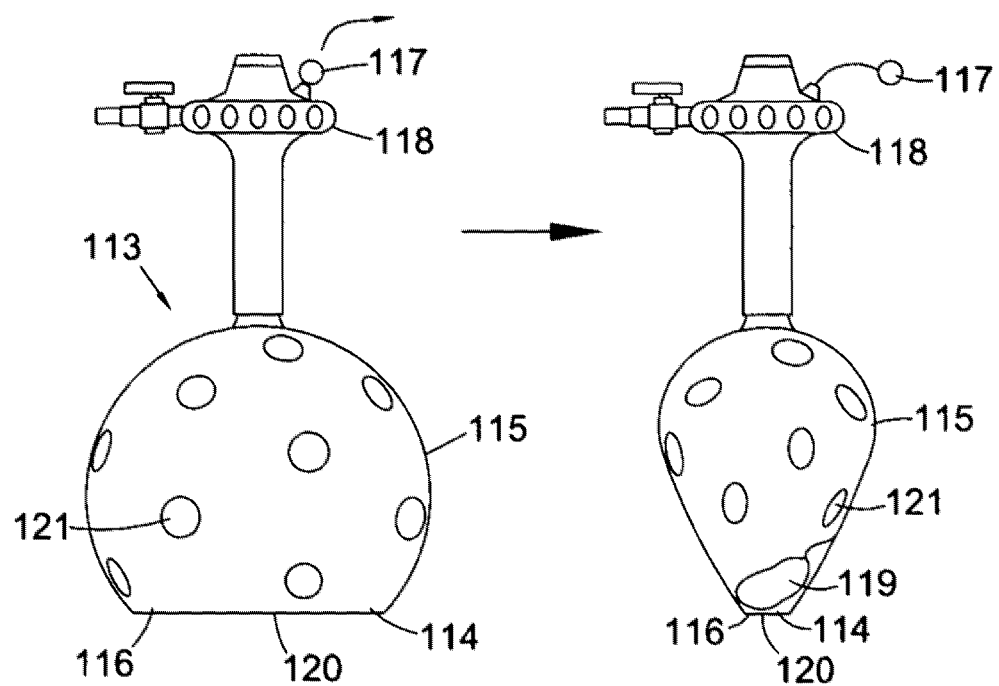
FIG. 11 illustrates steps in the use of a device according to a preferred embodiment of the present invention in a cholecystectomy procedure.

An exemplary procedure utilising a preferred embodiment of the device 113 of the present invention is illustrated in FIGS. 10 and 11. In this embodiment of the device 113 the lowermost rim 114 of the inflatable sheet 115 is circumscribed by a wire 116 which is connected to a puller 117 (visible in FIG. 11) linked to the collar 118. The device 113 is inserted and expanded as described above in relation to FIGS. 9A to 9D. A procedure is then carried out to resect diseased tissue or an organ 119 (e.g. the gallbladder) which is to be removed from surrounding tissue at the working site. The inflation fluid is then evacuated from the device 113 and the puller 117 is grasped and pulled away from the collar 118 so as to draw the wire 116 surrounding the rim 114 together, thereby closing the lower orifice 120 and enclosing the tissue or organ 119 within the internal cavity 121 of the now collapsed sheet section 115 of the device 113. The device 113 including the tissue or organ 119 can then be removed from the patient in a simple and convenient manner.

It will be appreciated that the device of the present invention may be used without any additional means to retract or support tissue or organs surrounding the intended working site as described above with reference to FIGS. 10 and 11, or it may be used in combination with any other suitable method for retracting or supporting neighbouring tissue or organs, such as $CO_2$ insufflation, which could, by way of example, be provided via the port to which the outer wall of the device is connected.

It will be understood that numerous modifications can be made to the embodiments of the invention described above without departing from the underlying inventive concept and that these modifications are intended to be included within the scope of the invention. For example, it will be appreciated that features of the different preferred embodiments of the present invention described above can be combined together in numerous different arrangements to suit a particular application while still being in accordance with the present invention.

The invention claimed is:

1. A device for retracting and supporting surrounding organs and tissues, thereby creating a working space within a human or animal body, the device comprising an outer wall having inner and outer layers of material, the device having a non-expanded condition and an expanded condition wherein said device is expanded to the expanded condition by introduction of fluid, between the inner and outer layers of material, in said expanded condition the device having a truncated generally spherical shape; in said expanded condition said outer wall defining a hollow body having an inner cavity in communication with an orifice, the inner cavity forming a working site within said inner cavity and adjacent said orifice such that, in use, said working site can be visualised and/or accessed via said inner cavity and said orifice, wherein the outer wall defines one or more pre-formed apertures for introduction of an instrument, the inner cavity having a greater size when the device is in the expanded condition relative to when the device is in the non-expanded condition and predefined regions of said outer wall consist of said inner and outer layers of material.

2. A device according to claim 1, wherein the outer wall is arranged to be inflatable so as to expand and adopt the expanded condition.

3. A device according to claim 2, wherein said outer wall is comprised of a plurality of individually inflatable segments.

4. A device according to claim 2, wherein the outer wall is configured so as to withstand inflation pressures of around 20 to 200 mmHg.

5. A device according to claim 1, wherein said outer wall consists of said inner and outer layers of material.

6. A device according to claim 1, wherein sections of the outer wall in between said predefined regions consist of a single layer of material and/or are non-inflatable.

7. A device according to claim 1, wherein said outer wall comprises a plurality of separate predefined regions, at least one of which adopts an elongate tubular shape upon the introduction of said fluid in between said inner and outer layers of material.

8. A device according to claim 1, wherein said predefined regions are in fluid communication so as to define a single elongate tubular shape upon the introduction of said fluid in between said inner and outer layers of material.

9. A device according to claim 8, wherein said single elongate tubular shape is arranged to assume a generally coiled configuration upon the introduction of said fluid in between said inner and outer layers of material.

10. A device according to claim 1, wherein the outer wall is substantially transparent, is configured such that upon expansion said hollow body has a generally spherical shape, and/or comprises a polymeric material.

11. A device according to claim 1, wherein a region of the outer wall adjacent the orifice is connected to a draw-cord which is operable to close said orifice.

12. A method for retracting and supporting surrounding organs and tissues, thereby creating a working space within a human or animal body using a device comprising an outer wall, the device having a non-expanded condition and an expanded condition, in said expanded condition the device having a truncated generally spherical shape, the outer wall comprising at least an inner and an outer layer of material and defining one or more pre-formed apertures for introduction of an instrument, wherein predefined regions of said outer wall consist of said inner and outer layers of material, the method comprising introducing the device into said human or animal body with the outer wall of the device in said non-expanded condition and then expanding the device, to the expanded condition by introduction of fluid between the inner and outer layers of material, such that it adopts said expanded condition and retracts and supports surrounding organs and tissues, the expanded device defining a hollow body having an inner cavity in communication with an orifice, the inner cavity forming a working site within said inner cavity and adjacent to the orifice such that said working site can be visualised and/or accessed via said inner cavity and said orifice, the inner cavity having a greater size when the device is in the expanded condition relative to when the device is in the non-expanded condition.

13. A method according to claim 12, wherein expansion of the device is effected by inflating said outer wall.

14. A method according to claim 12, wherein said fluid is introduced in between said inner and outer layers of material at a pressure of around 20 to 200 mmHg and/or at a temperature of around 15 to 40° C.

15. A method of performing a surgery comprising a method for creating a working space within a human or animal body according to claim 12 and performing a surgical procedure.

16. A method according to claim 15, wherein the surgery comprises intra-abdominal surgery, or laproscopic surgery.

17. A method according to claim 15, wherein the surgery comprises a cholycystectomy.

18. A method according to claim 17, wherein the cholycystectomy employs a device according to claim 11.

* * * * *